US010602752B2

(12) United States Patent
Thomas et al.

(10) Patent No.: US 10,602,752 B2
(45) Date of Patent: Mar. 31, 2020

(54) ANTI-REFLUX INFANT NUTRITION

(75) Inventors: Marie Thomas, Steenvoorde (FR);
Francis Lecroix, Steenvoorde (FR);
Evan Abrahamse, Wageningen (NL);
Houkje Bouritius, Wageningen (NL)

(73) Assignee: N.V. NUTRICIA, Zoetermeer (NL)

( * ) Notice: Subject to any disclaimer, the term of this patent is extended or adjusted under 35 U.S.C. 154(b) by 1370 days.

(21) Appl. No.: 13/264,704

(22) PCT Filed: Apr. 15, 2010

(86) PCT No.: PCT/NL2010/050192
§ 371 (c)(1),
(2), (4) Date: Mar. 5, 2012

(87) PCT Pub. No.: WO2010/120172
PCT Pub. Date: Oct. 21, 2010

(65) Prior Publication Data
US 2012/0213858 A1     Aug. 23, 2012

(30) Foreign Application Priority Data
Apr. 15, 2009  (EP) .................................. 09157995

(51) Int. Cl.
| A23C 9/137 | (2006.01) |
| A23L 29/20 | (2016.01) |
| A23L 29/238 | (2016.01) |
| A23L 29/25 | (2016.01) |
| A23L 33/19 | (2016.01) |
| A61K 47/36 | (2006.01) |
| A23C 9/123 | (2006.01) |
| A61K 38/17 | (2006.01) |
| A61K 38/01 | (2006.01) |
| A61K 9/00 | (2006.01) |
| A23L 33/00 | (2016.01) |

(52) U.S. Cl.
CPC ............ *A23C 9/1238* (2013.01); *A23L 29/20* (2016.08); *A23L 29/238* (2016.08); *A23L 29/25* (2016.08); *A23L 33/19* (2016.08); *A23L 33/40* (2016.08); *A61K 9/0095* (2013.01); *A61K 38/018* (2013.01); *A61K 38/1709* (2013.01); *A61K 47/36* (2013.01); *A23Y 2240/75* (2013.01)

(58) Field of Classification Search
None
See application file for complete search history.

(56) References Cited

U.S. PATENT DOCUMENTS

| 4,105,461 A | 8/1978 | Racciato |
| 4,542,035 A | 9/1985 | Huang et al. |
| 4,956,185 A * | 9/1990 | Cajigas ........................... 426/43 |
| 5,429,837 A | 7/1995 | Balabaud et al. |
| 5,597,603 A | 1/1997 | Cha et al. |
| 6,277,395 B1 | 8/2001 | Fukui et al. |
| 6,458,395 B1 | 10/2002 | Emoto |
| 6,461,589 B2 | 10/2002 | Robbins |
| 6,858,245 B2 | 2/2005 | De Coninck |
| 6,887,850 B2 | 5/2005 | Fuchs et al. |
| 2003/0072729 A1 | 4/2003 | Szymczak et al. |
| 2007/0104700 A1* | 5/2007 | Garcia-Rodenas ..... A23L 33/21 424/93.45 |
| 2007/0254062 A1* | 11/2007 | Singhal .................. A23L 33/40 426/2 |
| 2009/0074940 A1 | 3/2009 | Sliwinski |

FOREIGN PATENT DOCUMENTS

| EP | 0 611 525 B1 | 3/1997 |
| EP | 0 745 330 B1 | 10/1998 |
| EP | 1 166 645 A2 | 1/2002 |
| EP | 1 431 313 A1 | 6/2004 |
| EP | 1 433 383 A1 | 6/2004 |
| EP | 1 313 376 B1 | 12/2005 |
| EP | 1 930 407 A1 | 6/2008 |
| EP | 1 930 407 B1 | 11/2009 |
| FR | 2 699 370 A1 | 6/1994 |
| FR | 2 913 857 A1 | 9/2008 |
| FR | 2913857 A1 | 9/2008 |
| JP | 07-184569 A | 7/1995 |
| JP | 2000-191553 | 7/2000 |
| JP | 2003-245039 A | 9/2003 |
| KR | 200290193 A | 11/2002 |
| WO | WO-01/01789 A1 | 1/2001 |
| WO | WO-03/011051 A1 | 2/2003 |
| WO | WO-03/055334 A1 | 7/2003 |
| WO | WO-2004/006179 A1 | 1/2004 |
| WO | WO-2006/054886 A1 | 5/2006 |
| WO | WO-2009/012889 A1 | 1/2009 |

OTHER PUBLICATIONS

Sweet whey powder composition from Dairy for Global Nutrition website: http://www.dairyglobalnutrition.org, (2009).*
Blareau et al. (English machine translation of WO 1996/006924; 1996).*
All Ayurveda.com website (accessed at http://www.allayurveda.com/topic_month_april2009.asp) Apr. 2009 (of record).*
Anderson Erickson Products—Cultured Lowfat Buttermilk (accessed at http://www.aedairy.com/products/cultured-lowfat-buttermilk/, publication date Jan. 3, 2009; of record).*
Vandenplas et al (European Journal of Pediatrics, vol. 153, pp. 419-423; 1994) (of record).*
Huang et al., Cochrane Database of Systematic Reviews, Issue 3, Article No. CD003211 (2002) (of record).*
Miyazawa et al., Journal of Pediatric Gastroenterology and Nutrition, vol. 38, pp. 479-483 (May 2004) (of record).*
Blareau et al. (English machine translation of WO 1996/006924; 1996) (of record).*
Miyazawa, et al., "Effect of Locust Bean Gum in Anti-regurgitant Milk on the Regurgitation in Uncomplicated Gastroesophageal Reflux," Journal of Pediatric Gastroenterology and Nutrition, vol. 38, No. 5, pp. 479-483, May 2004, XP-002581159.

(Continued)

*Primary Examiner* — Sharmila G Landau
*Assistant Examiner* — Paul D. Pyla
(74) *Attorney, Agent, or Firm* — Gilberto M. Villacorta; Sunit Talapatra; Foley & Lardner LLP

(57) ABSTRACT

An infant formula for preventing gastro-esophageal reflux is disclosed comprising whey protein and/or casein, a galactomannan thickener, and a fermented milk-derived product.

10 Claims, No Drawings

(56) References Cited

OTHER PUBLICATIONS

Search Report in International Application PCT/NL2010/050192 dated Jul. 6, 2010.
Chau et al., "Chemical composition of three underutilized legume seeds grown in China," Science Direct, available on line Jun 23, 1998, 1 page.
Database WPI Section Ch, Week 200050, Derwent Publications Ltd., London, GB; AN 2000-545835 [XP002334602] & JP 2000 292553 A, Jul. 11, 2000, English abstract.
Database WPI Section Ch, Week 200413, Derwent Publications Ltd., London, GB; AN 2003-264413 [XP002334599] & KR 398 470 B, Sep. 19, 2003, English abstract.
Definition of terms "powder" and "milling" taken from The American Heritage Dictionary of the English Language, retrieved from "The Free Dictionary" online on Aug. 25, 2009.
Galactomannan from Wikipedia, retrieved from http://en.wikipedia.org/wiki/Galactomannan, Jun. 11, 2009.
Glucomannan from Wikipedia, retrieved from http://en.wikipedia.org/wiki/Glucomannan, last modified Oct. 15, 2010, 3 pages.
Material Safety Data Sheet Xanthan gum MSDS, Science Lab.com, Oct. 11, 2005, pp. 1-6.
Material Safety Data Sheet Xanthan gum MSDS, Science Lab.com, http://www.sciencelab.com/msds.php?msdsId=9927645, last updated Nov. 1, 2010, 6 pages.
"Nutrition Facts and Calories (kcal) per 100 g wheat starch," http://translate.googleusercontent.com/translate_c?hl=en&sl=de&u=http://gesuender-abnehmen.com/abneh . . . , Feb. 7, 2011, 4 pgs.
Nutrition Information for: Gums, microbial (xanthan gum), Fit Day, 2000, 2 pages.
Nutritional Information for: Gums, microbial (xanthan gum), FitDay, www.fitday.com/webfit/FoodFacts_outside.html?FoodID=42242&OwnerID=11, last viewed Feb. 5, 2011, 2 pages.
Tomlin et al., "The effect of feeding xanthan gum on colonic function in man: correlation with in vitro determinants of bacterial breakdown," PubMed, PMID: 8329363, 1993, 1 page.
Xanthan Gum product material, C.E. Roeper GmbH, http://www.roeper.de/en/produktdetail.html?nummer=1851, last viewed Feb. 5, 2011, 2 pages.
Final Office Action in U.S. Appl. No. 11/719,577, dated Jan. 14, 2011.
"Simply Thick—the thickening gel you can't taste", available online as of Jun. 2002 from www.simplythick.com, p. 1.
"identification and Management of Dysphagia in Children with Neurological Impairment" Best Practice (2000), vol. 4, Issue 3, pp. 1-3.
"Starch" Virtual Chembook, Elmhurst College, Available Mar. 23, 2015 from www.elmhurst.edu.

* cited by examiner

ANTI-REFLUX INFANT NUTRITION

FIELD OF THE INVENTION

The present invention is in the field of anti-reflux nutrition. The invention is particularly advantageous for infants.

BACKGROUND OF THE INVENTION

Gastro-esophageal reflux (GER) is the backward flow of stomach contents up the esophagus and sometimes even into or out of the mouth. At the lower end of the esophagus, the lower esophageal sphincter (LES) opens when food is swallowed and then normally closes again to keep stomach contents in place.

When the LES is not working properly, with GER the stomach content including hydrochloric acid, comes into contact with the esophagus, throat, nasal cavities, lungs and/or teeth, causing pain and damage. Over time, repeated exposure of these areas with acid can cause increasing damage and cause more serious complications.

At least 50% of infants are born with some degree of GER due to immaturity of the LES. Most of these infants will not have major complications and will outgrow it before they are a year old. It is estimated that about 3% will not outgrow it and will experience the more serious complications related to gastro-esophageal reflux disease (GERD).

Hence, GER(D) is especially a problem during infancy. Besides the already above mentioned problems, GER(D) in infants may result in dehydration, impaired growth and/or a failure to thrive of the infant.

Nutrilon A.R. 1 is a commercially available infant formula intended for infants having GER. It comprises 0.4 g per 100 ml of the thickener locust bean gum. It comprises 1.6 g protein per 100 ml with a weight ratio of casein to whey protein of 8 to 2.

Gallia A.R. 1 is a commercially available infant formula comprising 0.5 g per 100 ml of the thickener locust bean gum. It is intended for infants suffering from GER. It comprises 1.6 g protein with a weight ratio casein to whey protein of 6 to 4.

EP 0 745 330 discloses an infant formula containing as thickening agents useful for treating regurgitation potato starch, waxy grain starch (e.g. waxy corn starch, waxy rice starch) or a mixture thereof. Disadvantageously starch replaces lactose as digestible carbohydrate source, which is not desired since lactose is the main source of digestible carbohydrates in human milk. Moreover, starch is degradable by alpha-amylase and therefore less efficient as thickener.

EP 0 611 525 discloses a milk for infants that is prepared by pre-heating, addition of 0.3-1% (based on total weight of the sterilised, packaged milk) of carob, guar, carrageen and/or pectins, as thickeners, homogenisation, treating at ultra high temperature, and packaging.

FR 2913857 discloses the preparation of anti-regurgitation infant milk in powder form and an infant milk powder comprising 1-5 wt. % based on dry weight of carob flour.

JP2003245039 discloses a gastro-esophageal reflux suppressing formula milk suitable for dietetic therapy of infant gastro-esophageal reflux diseases, the viscosity of which is low when dissolved, and increased after suckled.

EP 1 930 407 A1 discloses *Bifidobacterium bifidum* which has an effect of killing *Helicobacter pylori* and shows high survivability even in the case of being stored in a fermented milkfood or drink under aerobic condition.

SUMMARY OF THE INVENTION

The present inventors surprisingly found that an infant milk formula (IMF) comprising a fermented milk-derived product, in particular milk fermented with *Streptococcus thermophilus*, and a galactomannan thickener, in particular locust bean gum, resulted in a more thickened product, in particular more thickened in the stomach.

A beneficial consequence of the present finding is that the amount of LBG in the infant nutrition product can be decreased compared to conventional compositions, while maintaining the advantageous anti-reflux properties of the state of the art IMF.

This offers several advantages, among others because i) LBG is expensive, ii) the presence of LBG imposes a risk on bacterial infections, as the sources of galactomannans are often bacterially contaminated and difficult to sterilize without degrading the product and iii) reducing the amount of LBG allows the addition of other fibers, in particular non-digestible oligosaccharides (NDO). Normally no NDO is added to LBG containing infant formula in order to keep the load of fibers below a certain upper level. Especially an excessive fiber load may result in abdominal discomfort such as bloating and cramps. With a reduced LBG content prebotics, e.g. NDO, can be added which have selectively better effects on for example bifidogenicity than LBG. Co-administration of for example trans galacto-oligosaccharides (TOS) and/or fructo-oligosacchardies (FOS) in the LBG containing formula will further decrease abdominal cramps, pain, bloating etc which is especially beneficial for infants suffering from or at risk of GER.

Also an advantage of reducing the amount of LBG is that iv) the amount of casein and/or ratio of casein to whey protein can be reduced. Up to now casein was normally present in anti-reflux formulae at relatively high ratio of 1 or above. Consumption of casein results in the formation of coarse curd in the stomach which is beneficial in preventing GER. The present finding enables to have a whey protein to casein ratio more reminiscent to that observed in human milk (being 6 to 4). This results in an improved amino acid profile more comparable to human milk and hence a protein content that can be reduced to levels more reminiscent to levels found in human milk without impairment of growth. Another consequence may be that that the amount of protein based on total energy can be reduced. In this way the protein concentration will advantageously be more close to the protein concentration in human milk.

DETAILED DESCRIPTION OF THE INVENTION

The present invention thus concerns a method for prevention of gastro-esophageal reflux and/or a method for prevention and/or treatment of gastro-intestinal reflux disease, said method comprising the administration of a nutritional composition comprising a) whey protein and/or casein, b) a thickener selected form the group consisting of locust bean gum, tara gum, gum tragacanth, guar gum, and fenugreek gum and c) a fermented milk-derived product.

In other words the present invention concerns the use of a thickener for the preparation of a nutritional composition for prevention of gastro-esophageal reflux and/or for prevention and/or treatment of gastro-intestinal reflux disease, wherein said nutritional composition comprises a) whey protein and/or casein, b) said thickener selected form the group consisting of locust bean gum, tara gum, gum tragacanth, guar gum, and fenugreek gum and c) a fermented milk-derived product.

The invention can also be worded as a nutritional composition for use in prevention of gastro-esophageal reflux and/or for prevention and/or treatment of gastro-intestinal reflux disease, said composition comprising a) whey protein and/or casein, b) a thickener selected form the group consisting of locust bean gum, tara gum, gum tragacanth, guar gum, and fenugreek gum and c) a fermented milk-derived product.

In a further aspect the present invention provides a nutritional composition comprising a) whey protein and/or casein, b) a thickener selected form the group consisting of locust bean gum, tara gum, gum tragacanth, guar gum, and fenugreek gum and c) a fermented milk-derived product.

In a preferred embodiment, the present invention is for providing nutrition to infants or the present composition is for use in providing nutrition to infants.

Gastroesophageal Reflux

Gastroesophageal reflux (GER) is the backward flow of stomach contents up the esophagus. In infants GER can range from reflux material simply entering the distal (bottom of the) esophagus to spitting up and even frequent projectile vomiting. Regurgitation, heartburn or acid reflux as also forms of GER. Gastro Esophageal Reflux disease (GERD) is a form of gastro-esophageal reflux where severe complications arise. GERD is a pathological process and the complications can be typical, e.g. failure to thrive, feeding and oral aversions, esophagitis, etc, or atypical, e.g. wheezing, pneumonia, chronic sinusitis, etc. Patients with GERD have complications arising from their GER that necessitate medical intervention. GERD is also referred to as "Pathogenic GER".

Fermented Milk-Derived Product

The present composition comprises a fermented milk-derived product. This fermented milk-derived product is obtained by incubation of a combination of milk, e.g. skim milk, or a milk derived product, e.g. lactose, with at least one microorganism, preferably *Streptococcus thermophilus*. Preferably the combination is incubated for 10 minutes to about 6 hours. The temperature during incubation is preferably between 20 and 50° C. After incubation the incubated product is preferably subjected to a heat treatment. By this heat treatment preferably at least 90% of living microorganisms are inactivated. The heat treatment preferably is performed at a temperature between 80 and 180° C. Procedures to prepare fermented milk-derived products suitable for the purpose of the present invention are known per se. EP 778885, which is incorporated herein by reference, discloses in particular in example 7 a suitable process for preparing a fermented milk-derived product. FR 2723960, which is incorporated herein by reference, discloses in particular in example 6 a suitable process for preparing a fermented milk-derived product.

Briefly, a milk derived product, preferably pasteurised, containing lactose and optionally further macronutrients such as (vegetable) fats, casein, whey protein, vitamins and/or minerals etc. is concentrated, e.g. to between 15 to 50% dry matter and then inoculated with *S. thermophilus*, for example with 5% of a culture containing $10^6$ to $10^{10}$ bacteria per ml. Temperature and duration of fermentation are as mentioned above. Suitably after fermentation the fermented milk-derived product may be pasteurised or sterilized and for example spray dried or lyophilised to provide a form suitable to be formulated in the end product further containing galactomannan thickener.

The bacterial strains of *S. thermophilus* that are preferably used to prepare the fermented milk-derived product for the purpose of the present develop beta-galactosidase activity in the course of fermentation of the substrate. Preferably beta-galactosidase activity develops in parallel with acidity. Preferably a beta-galactosidase activity develops which is sufficient to permit subsequent enrichment of the fermented milk-derived product in galacto-oligosaccharides. Thus preferably suitable *S. thermophilus* strains, when cultured on a medium containing lactose, in particular a medium based on milk concentrate, achieve fermentation of the medium accompanied by high production of galacto-oligosaccharides. Selection of a suitable strain of *S. thermophilus* is described in example 2 of EP 778885 and in example 1 of FR 2723960. A preferred strain of *S. thermophilus* is then selected that with a developing beta-galactosidase activity also produce galacto-oligosaccharides.

Preferred strains of *S. thermophilus* to prepare the fermented milk-derived products for the purpose of the present invention have been deposited by Compagnie Gervais Danone at the Collection Nationale de Cultures de Microorganismes (CNCM) run by the Institut Pasteur, 25 rue du Docteur Roux, Paris, France on 23 Aug. 1995 under the accession number I-1620 and on 25 Aug. 1994 under the accession number I-1470.

Preferably, in the preparation of the fermented milk-derived product additionally other strains of lactic acid bacteria are present or, either simultaneously or consecutively, the fermented milk-derived product additionally is fermented by other strains of lactic acid bacteria. Other strains of lactic acid bacteria are preferably selected from the group consisting of *Lactobacillus* and *Bifidobacteria*, more preferably *Bifidobacterium breve*, most preferably *Bifidobacterium B. breve* strain deposited by Compagnie Gervais Danone at the CNCM under number I-2219 on 31 May 1999.

The present composition preferably comprises 5 to 100 wt. % based on dry weight of the total product, of the fermented milk-derived product. In one embodiment the present composition preferably contains 5 to 70 wt. %, preferably 10-40 wt. %, based on dry weight of the total product, of the fermented milk-derived product. In one embodiment the present composition preferably contains 20 to 100 wt. %, preferably 50 to 100 wt. %, even more preferably 50 to 95 wt. % based on dry weight of the total product, of the fermented milk-derived product. Higher concentrations of fermented product advantageously improve the viscosity on the stomach.

Gallactomannan

The present composition preferably comprises less than 4 g galactomannan thickener per 100 g dry weight of the total product, preferably less than 3 g, preferably from about 0.3 to less than 3 g, preferably less than 2.5 g galactomannan thickener per 100 g dry weight of the total product, more preferably between 0.3 and 2 g, even more preferably between 0.3 and 1.5 g galactomannan thickener, per 100 g dry weight of the total product. The present composition preferably comprises less than 0.5 g galactomannan thickener per 100 ml liquid product, preferably less than 0.3 g, preferably from about 0.04 to less than 0.3 g galactomannan thickener per 100 ml liquid product. In a preferred embodiment the galactomannan thickener is Locust Bean Gum (LBG).

Locust Bean Gum (LBG), also referred to as Carob Bean Gum is a product of the tree *Ceratonia siliqua* of the family Leguminous. The carob tree produces long pods that upon removal of the outer husk and central germ expose the layer of endosperm. It is this endosperm that is normally the source of the desired gum. Locust Bean Gum is known to be a galactomannan. Galactomannans usually are defined as polysaccharides consisting of a mannose backbone with galactose side groups. More specifically, the present LBG can be described as a (1-4)-linked beta-D-mannan backbone with branchpoints from 6-positions linked to alpha-D-galactose, i.e. 1-6-linked alpha-D-galactose side groups.

A number of grades of LBG are available, and for each grade it is possible to have different particle sizes according to the requirements of the end user. In the context of the present invention, preferably LBG powder is used, wherein less than 20 wt. % of the LBG particles has a particle size larger than 200 micrometer, preferably less than 10 wt. % has a particle size larger than 200 micrometer.

Non-Digestible Oligosaccharides

The composition according to the present invention preferably comprises non-digestible oligosaccharides as opposed to sucrose, lactose, maltose and not further specified maltodextrins which are considered digestible. Non-digestible oligosaccharides preferably stimulate the growth of the intestinal lactic acid producing bacteria, particularly *Bifidobacteria* and/or the *Lactobacilli*. Preferably the non-digestible oligosaccharide is a neutral oligosaccharide. The term "neutral oligosaccharide" as used in the present invention refers to oligosaccharides wherein more than 75% of the saccharide units are selected from the group consisting of glucose, fructose, galactose, mannose, ribose, rhamnose, arabinose, and xylose, preferably more than 85%, more preferably more than 95%, even more preferably more than 99%. Preferably the present non-digestible oligosaccharide is soluble. The term "soluble" as used herein, when having reference to a polysaccharide, fiber or oligosaccharide, means that the substance is at least soluble according to the method described by L. Prosky et al., J. Assoc. Off. Anal. Chem. 71, 1017-1023 (1988).

Preferably the present composition comprises at least one non-digestible oligosaccharide selected from the group consisting of galacto-oligosaccharides, non-digestible dextrins, xylo-oligosaccharides, arabino-oligosaccharides, gluco-oligosaccharides (such as gentio-oligosaccharides and cyclodextrins), chito-oligosaccharides, fuco-oligosaccharides, manno-oligosaccharides, isomalto-oligosaccharides fructo-oligosaccharides (such as inulin), galactomanno-oligosaccharides, glucomanno-oligosaccharides, and arabinogalacto-oligosaccharides.

As a result of the fermentation process, the fermented milk-derived product that is included according to the present invention may already contain galacto-oligosaccharides. Hence, in one embodiment the present composition comprises at least one non-digestible oligosaccharide other than galacto-oligosaccharide. Preferably the present composition comprises at least fructo-oligosaccharides. The term "fructo-oligosaccharide" as used herein refers to a non-digestible polysaccharide carbohydrate comprising a chain of at least 2β-linked fructose units, with a DP of 2 to 250, preferably 7 to 100, more preferably 20 to 60. Preferably inulin is used. Inulin is available under the tradename "Raftilin HP®", (Orafti). The average DP of the present fructo-oligosaccharide is preferably at least 7, more preferably at least 10, preferably below 100. Other terms for fructo-oligosaccharides include inulin, fructopolysaccharide, polyfructose, fructans and oligofructose. The present composition preferably comprises fructo-oligosaccharides with a DP of 2 to 100.

In one embodiment the present composition comprises 3 to 9 wt. % non-digestible oligosaccharides, more preferably 3 to 6 wt. %, based on dry weight of the total composition The present composition preferably comprises at least two non-digestible (neutral) oligosaccharides with different average degrees of polymerization (DP). Preferably the weight ratios:

a. (non-digestible (neutral) oligosaccharides with DP 2 to 5):(non-digestible (neutral) oligosaccharides with DP 6, 7, 8, and/or 9)>1; and/or b. (non-digestible (neutral) oligosaccharides with DP 10 to 60):(non-digestible (neutral) oligosaccharides with DP 6, 7, 8, and/or 9)>1

Preferably both weight ratios are above 2, even more preferably above 5.

For further improvement, the present non-digestible oligosaccharide preferably has a relatively high content of short chain oligosaccharides, as these strongly stimulate the growth of *Bifidobacteria*. Hence, preferably at least 10 wt. % of the non-digestible oligosaccharides in the present composition has a DP of 2 to 5 (i.e. 2, 3, 4, and/or 5) and at least 5 wt. % has a DP of 10 to 60. Preferably at least 50 wt. %, more preferably at least 75 wt. % of the non-digestible neutral oligosaccharides have a DP of 2 to 9 (i.e. 2, 3, 4, 5, 6, 7, 8, and/or 9).

As already mentioned, the present composition may also contain galacto-oligosaccharides as a result of the fermentation process of the milk-derived product, in particular as a result of the action of *S. thermophilus*. Usually galacto-oligosaccharides obtained upon fermentation with *S. thermophilus* are galacto-oligosaccharides comprising saccharide units that are beta-1,3-linked. Thus the present composition in one embodiment contains beta-1,3-linked galacto-oligosaccharides.

Viscosity

The viscosity of the present composition was determined using a starch-paddle-geometry in a concentric-cylinder with a modular compact rheometer (Physica, MCR 300, Anton Paar Benelux) at a temperature of 37° C. and at a shear rate of 10 $s^{-1}$. The viscosity was determined of the nutritional composition that is ready to drink at a pH of about neutral, e.g a pH of about 7±0.5. Also the viscosity was determined under conditions resembling a baby's stomach, in particular at pH about 5. To this end 13 g of powdered nutritional composition was dissolved in 90 g water. Of one part the pH was left unchanged; of another part the pH was lowered to 5.0. All samples were put at 37° C. for 1 hr.

In one embodiment, the present nutritional composition at neutral pH has a viscosity of above 30 mPas·s and preferably below 80 mPa·s at a temperature of 37° C. and at a shear rate of 10 $s^{-1}$.

In one embodiment the present nutritional composition at pH 5.0 has a viscosity of above 80 mPa·s, preferably above 100 mPa·s. Preferably the present nutritional composition at pH 5 has a viscosity below 300 mPa·s and even more preferably below 250 mPa·s.

Whey Protein and Casein

The present composition comprises whey protein and/or casein. Preferably the present composition comprises whey protein and casein. The whey protein and/or casein in the present composition includes the whey protein and/or casein that is present in the fermented milk-derived product. In one embodiment the whey protein and/or casein is partially hydrolysed.

In view of the advantageous thickening properties of the present composition, the thickening effect of coagulating casein in the stomach is not a necessity anymore. As a consequence, compared to conventional anti-reflux formula, the amount of casein can be reduced in the composition according to the present invention.

Advantageously the reduction in the amount of casein can be translated into an overall reduction of the protein content of the present nutritional composition, making it more similar to the protein content found in human milk. Hence in one embodiment, the present composition comprises less than 1.6 g protein per 100 ml liquid product, preferably less than 1.5 g. In one embodiment of the present composition the sum of casein and whey protein is less than 15 wt. % based on dry weight of the total composition, more preferably less than 10 wt. %.

Hence in one embodiment the present invention concerns a nutritional composition comprising a) whey protein and/or casein; wherein the sum of whey protein and casein is less than 15 wt. % based on dry weight of total composition, b) a thickener selected form the group consisting of locust bean gum, tara gum, gum tragacanth, guar gum, and fenugreek gum; and c) 5 to 100 wt. % based on dry weight of the total product, of a fermented milk-derived product.

Alternatively the reduction in the amount of casein allows the use of an increased amount of whey protein, which is advantageous in view of the high nutritional value of whey protein. Hence, in one embodiment of the present composition the weight ratio casein to whey protein is 1 or less, preferably is below 1. In a preferred embodiment the weight ratio casein to whey protein is about 0.67, which is comparable to the ratio found in human milk.

Other Macronutrients

The present composition preferably comprises fat in conventional amounts for anti-reflux or anti-regurgitation formula. Preferably the present composition comprises vegetable fat. Preferably the present composition comprises linoleic acid (LA; 18:2 n6) and alpha-linolenic acid (ALA; 18:3 n3).

The present composition preferably comprises digestible carbohydrates in conventional amounts for anti-reflux or anti-regurgitation formula. Preferably the present composition comprises digestible carbohydrates. Preferably the present composition comprises lactose.

In one aspect the invention concerns a nutritional composition comprising protein, lipids and carbohydrates and comprising a) whey protein and/or casein; wherein the sum of whey protein and casein is less than 15 wt. % based on dry weight of total composition, b) a thickener selected form the group consisting of locust bean gum, tara gum, gum tragacanth, guar gum, and fenugreek gum; and c) 20 to 100 wt. % based on dry weight of the total product, of a fermented milk-derived product. All the preferred embodiments mentioned here above, especially with respect to origin and nature of the fermented milk-derived product, gallactomannan, non-digestible oligosaccharides, viscosity, whey protein and casein and nature of other macronutrients also apply to this aspect of the invention.

Application

The present composition is preferably used for prevention of gastro-esophageal reflux and/or for prevention and/or treatment of gastro-intestinal reflux disease. Gastro-esophageal reflux (GER) is the backward flow of stomach contents up the esophagus and sometimes even into or out the mouth. At the lower end of the esophagus, the lower esophageal sphincter (LES), opens when food is swallowed, and then normally closes again to keep stomach contents in place.

The present composition is preferably administered to infants with an age between 0-12 months, more preferably 0-6 months. Preferably the present composition is administered to infants with an immature LES.

EXAMPLES

Example 1 Preparation of Fermented Milk-Derived Product

Vegetable fat was added to cow's milk heated at 75° C. The mixture was homogenised in two stages, the first one at 200 kg·s/cm$^2$, the second at 50 kg·s/cm$^2$. Aqueous solutions of lactose and maltodextrin and vitamins and minerals were added. The composition was pasteurised at 115° C. and concentrated by evaporation to 48% dry material. The concentrate was cooled to 37° C. and inoculated with 5% of a culture of *S. thermophilus* I-1470 containing 10$^8$ bacteria/ml and incubated for 5.5 h at 44° C. The fermented milk-derived product was then spray dried.

Example 2

Packaged infant formula, intended for infants of 0 to 6 m of age comprising per 100 ml: 70 kcal; 3.1 g fat (vegetable fat); 1.4 g protein (0.6 g whey protein, 0.8 g casein); 9.1 g digestible carbohydrates (over 50% lactose); 0.4 g locust bean gum; 15 wt. % of a fermented product obtained by the method as described in example 1; minerals, trace elements, vitamins, carnitine, taurine, inositol and choline are present in amounts as known in the art.

The package is labeled with the text "Anti-regurgitation".

Example 3

Infant formula, intended for infants of 0 to 6 m of age comprising per 100 ml: 70 kcal; 3.1 g fat (vegetable fat); 1.4 g protein (0.6 whey protein, 0.8 casein); 9.1 g digestible carbohydrates (over 50% lactose); 0.25 g locust bean gum; 15 wt. % of a fermented product obtained by the method as described example 1; minerals, trace elements, vitamins, carnitine, taurine, inositol and choline are present in amounts as known in the art.

Example 4

Infant formula, intended for infants of 0 to 6 months of age comprising per 100 ml: 70 kcal; 3.1 g fat (vegetable fat); 1.4 g protein (0.6 whey protein, 0.8 casein); 9.1 g digestible carbohydrates (over 50% lactose); 0.4 g locust bean gum; 50 wt. % of a fermented product obtained by the method as described example 1; minerals, trace elements, vitamins, carnitine, taurine, inositol and choline are present in amounts as known in the art.

Example 5 Effect of a Combination of Fermented Product and Locust Bean Gum on Viscosity The effects of the presence or absence of a fermented product on the viscosity increasing effects of locust bean gum was tested. Locust bean gum (Meyprodin 200, Danisco) was added in various concentrations to a standard infant formula (Gallia 1, pH 6.8) or to a commercially available infant formula comprising fermented product (Lactofidus, pH 5.7). Viscosity was measured at 37° C. at 100 s$^{-1}$ by Thermo Haake VT 5550 equipment. In table 1 is shown that, at the same concentration of LBG, the viscosity is higher in an infant formula with fermented product than in standard IMF not comprising a fermented product.

TABLE 1

Viscosity increase dependent on locust bean gum concentration in standard IMF or in IMF comprising fermented product.

| Concentration LBG (wt %, based on dry weight of the composition) | Viscosity with Gallia 1 mPa · s | Viscosity with Lactofidus mPa · s |
|---|---|---|
| 0 | <2 | <2 |
| 1.5 | 7 | 9 |
| 2.35 | 15 | 29 |
| 2.7 | nd | 58 |
| 3 | 42 | 80 |
| 3.3 | 78 | 78 |

In table 2 the effect of the concentration of fermented product in the IMF on viscosity is shown, keeping a constant amount of locust bean gum (3 wt. %). The amount of fermented product was varied by mixing a non-fermented IMF (Gallia 1) with a fermented IMF (Lactofidus) in different weight ratio's. Viscosity was measured as above. It is shown that, at a constant value of LBG, an increasing amount of fermented product will result in an increased viscosity.

TABLE 2

Effect of concentration of fermented product in an IMF with LBG on viscosity.

| Amount of fermented IMF in wt. % based on total IMF without LBG | Viscosity mPa · s |
|---|---|
| 0 | 45 |
| 50 | 48 |
| 75 | 57 |
| 100 | 80 |

These results are indicative for the improved affect of a fermented product and a gallactomannan thickener on viscosity.

Example 6 Viscosity Measurement of IMF in the Bottle

An experiment was performed to evaluate the time course of viscosity in an IMF in the bottle. Viscosity was measured by a MCR 300 rheometer from Anton Paar (Courtaboeuf, France) with a geometry plan-plan 50, a gap of 2 mm at 10 s$^{-1}$ and 37° C. Samples were taken at 0, 15, 30, 45 and 60 minutes after reconstitution. The IMFs tested were:
1. An anti-reflux formula of the present invention comprising 15% fermented IMF (Lactofidus) and 85 wt % unfermented product (Gallia 2), based on dry weight of the composition without LBG, 0.42 g LBG per 100 ml, and 1.4 g protein per 100 ml with a casein to whey protein weight ratio of 6/4.
2. An anti-reflux formula of the state of the art (Gallia AR 2), not comprising fermented product, containing 0.47 g LBG per 100 ml, and 1.74 g protein per 100 ml with a casein to whey protein weight ratio of 6/4
3. An anti-reflux formula of the state of the art (Enfamil AR 2) not comprising fermented product, 2.2 g rice starch as thickener per 100 ml, and 1.7 g protein per 100 ml with a casein to whey protein weight ratio of 8/2.

The results are shown in Table 3. Since LBG, protein, and casein to whey ratio were not similar, only the relative development is shown with the value of the particular formula at time=0 set at 1. From Table 3 it can be deduced that compared to the old AR formula with LBG and without ferment, less viscosity is developed in the bottle. This is advantageous, since a low viscosity in the bottle makes it easier to drink and pass the hole in the teat. The viscosity of the products without LBG (Gallia 2 and Lactofidus) were <2 mPa·s.

TABLE 3

Viscosity development in the bottle

| time | A.R. IMF with fermented product and LBG | A.R. IMF with LBG | A.R. IMF with starch |
|---|---|---|---|
| 0 | 1$^a$ | 1$^a$ | 1$^a$ |
| 15 | 2.31 | 3.29 | 1.68 |
| 30 | 2.47 | 3.93 | 1.85 |
| 45 | 2.53 | 4.15 | 1.75 |
| 60 | 2.76 | 4.19 | 1.83 |

$^a$Viscosity was 35.6, 48.8, and 47.1 mPa · s at t = 0

Example 7 Viscosity Measurement of IMF Under Stomach Conditions

An experiment was performed to evaluate the time course of viscosity in an IMF in the stomach of an infant. Viscosity was measured as in example 6 at time 0, 15, 30, 45, 75 and 90 minutes after reconstitution.

The IMFs viscosity was followed under conditions mimicking the conditions in the stomach of an infant aged 4-12 m old. Basically to 210 ml IMF at 37° C. 20 ml saliva juice is added (comprising per I 600 mg alpha-amylase, 6.2 g NaCl, 2.2 g KCl, 0.22 g CaCl$_2$, 1.2 g NaHCO$_3$, pH 6.3), after 5 minutes stomach juice is added continuously at an amount of 75 ml during 90 minutes (comprising per 1100 mg pepsin, 140 mg lipase, 3.1 g NaCl, 1.1 g KCl, 0.11 g CaCl$_2$, pH 5.0) The pH was regulated by adding HCl or NaHCO$_3$. The pH was set to drop to a value of 3.5 at t=90. The IMFs tested are described in example 6.

The results are shown in Table 4. Since LBG, protein, and casein to whey ratio were not similar, only the relative development is shown with the value of the particular formula at time=0 set at 100%. From Table 4 it can be deduced that compared to the old AR formula with LBG and without ferment and compared to AR formula comprising starch, the viscosity increases in time and remains higher during the first 75 minutes, especially during the first 60 minutes, more particular during the first 30 minutes. This is advantageous, since maintenance of a higher viscosity for a longer period of time in the stomach will have positive effects on preventing gastro-esophageal reflux. Especially the period 60 minutes, more particular the first 30 minutes are the most important, since the majority of reflux happening during this time.

TABLE 4

Viscosity under stomach conditions

| Time (min) | A.R. IMF with ferment and LBG | A.R. IMF with LBG | A.R. IMF with starch |
|---|---|---|---|
| 0 | 100$^a$ | 100$^a$ | 100$^a$ |
| 15 | 113 | 86 | 74 |
| 30 | 66 | 39 | 44 |
| 45 | 45 | 27 | 29 |
| 60 | 28 | 21 | 8 |
| 75 | 19 | 11 | 2 |
| 90 | 5 | 5 | 2 |

$^a$viscosity was 69.2, 139 and 71.9 mPa · s at t = 0

The invention claimed is:

1. A method for reducing regurgitation or reflux of a nutritional composition, comprising administering to a patient suffering from gastro-esophageal reflux and/or disease a nutritional composition comprising:
   (a) whey protein and/or casein;
   (b) locust bean gum in an amount less than 4 g per 100 g dry weight; and
   (c) a fermented milk-derived product,
   wherein the composition as a liquid has a viscosity of (i) 80 mPa·s or higher at a pH of about 5.0 at 37° C. and a shear rate of 10 s$^{-1}$ or (ii) between 30 and 80 mPa·s at neutral pH at 37° C. and a shear rate of 10 s$^{-1}$; and wherein the composition comprises less than 1.5 g protein per 100 ml liquid product.

2. The method according to claim 1, wherein the patient is an infant.

3. The method according to claim 1, wherein the nutritional composition comprises 5 to 70 wt. % fermented milk-derived product based on dry weight of the total product.

4. The method according to claim 1, wherein the sum of whey protein and casein is less than 15 wt. % based on dry weight of the total composition.

5. The method according to claim 1, wherein the weight ratio casein to whey protein is below 1.

6. The method according to claim 1, wherein the nutritional composition comprises less than 2.5 g thickener per 100 g dry weight and/or less than 0.5 g thickener per 100 ml.

7. The method according to claim 1, wherein the composition further comprises non-digestible oligosaccharides.

8. The method according to claim 7, wherein the composition comprises at least one non-digestible oligosaccharides selected from the group consisting of galacto-oligosaccharides, non-digestible dextrins, xylo-oligosaccharides, arabino-oligosaccharides, gluco-oligosaccharides, chito-oligosaccharides, fuco-oligosaccharides, manno-oligosaccharides, isomalto-oligosaccharides fructo-oligosaccharides, galactomanno-oligosaccharides, glucomanno-oligosaccharides, and arabinogalacto-oligosaccharides.

9. The method according to claim 7, wherein the composition comprises 3 to 9 g non-digestible oligosaccharides per 100 g dry weight of the total composition.

10. The method according to claim 1, wherein the fermented milk-derived product comprises a product fermented by a strain of *Streptococcus thermophilus* with CNCM accession number I-1470 or I-1620.

* * * * *